US00PP25211P2

(12) United States Plant Patent
Beers

(10) Patent No.: US PP25,211 P2
(45) Date of Patent: Jan. 6, 2015

(54) ***CELOSIA* PLANT NAMED 'ZANCETOPICSUN'**

(50) Latin Name: *Celosia hybrida*
Varietal Denomination: Zancetopicsun

(71) Applicant: Catharina Maria Beers, Hoofddorp (NL)

(72) Inventor: Catharina Maria Beers, Hoofddorp (NL)

(73) Assignee: Chrysanthemum Breeders Association Research B.V., Rijsenhout (NL)

( * ) Notice: Subject to any disclaimer, the term of this patent is extended or adjusted under 35 U.S.C. 154(b) by 201 days.

(21) Appl. No.: 13/694,214

(22) Filed: Nov. 7, 2012

(51) Int. Cl.
*A01H 5/00* (2006.01)

(52) U.S. Cl.
USPC ..... Plt./263.1

(58) Field of Classification Search
USPC ..... Plt./263.1
See application file for complete search history.

(56) References Cited

U.S. PATENT DOCUMENTS

PP19,300 P2 * 10/2008 Beers ..... Plt./263.1

* cited by examiner

*Primary Examiner* — Wendy C Haas
(74) *Attorney, Agent, or Firm* — C. A. Whealy

(57) ABSTRACT

A new and distinct cultivar of *Celosia* plant named 'Zancetopicsun', characterized by its compact and upright plant habit; freely branching habit; dark green-colored leaves; freely flowering habit; bright yellow-colored flowers arranged on cristate-type inflorescences; and good garden performance.

2 Drawing Sheets

Botanical designation: *Celosia hybrida.*
Cultivar denomination: 'ZANCETOPICSUN'.

BACKGROUND OF THE INVENTION

The present invention relates to a new and distinct cultivar of *Celosia* plant, botanically known as *Celosia hybrida* and hereinafter referred to by the name 'Zancetopicsun'.

The new *Celosia* plant is a product of a planned breeding program conducted by the Inventor in Hillegom, The Netherlands. The objective of the breeding program is to create new compact and uniform *Celosia* plants with attractive flower coloration.

The new *Celosia* plant is a naturally-occurring whole plant mutation of *Celosia hybrida* 'Zancetopicyel', not patented. The new *Celosia* plant was discovered and selected by the Inventor as a single flowering plant within a population of plants of 'Zancetopicyel' in a controlled greenhouse environment in Rijsenhout, The Netherlands on May 24, 2010.

Asexual reproduction of the new *Celosia* plant by cuttings in a controlled greenhouse environment in Rijsenhout, The Netherlands since Jun. 28, 2010 has shown that the unique features of this new *Celosia* plant are stable and reproduced true to type in successive generations.

SUMMARY OF THE INVENTION

Plants of the new *Celosia* have not been observed under all possible environmental conditions and cultural practices. The phenotype may vary somewhat with variations in environmental such as temperature and light intensity without, however, any variance in genotype.

The following traits have been repeatedly observed and are determined to be the unique characteristics of 'Zancetopicsun'. These characteristics in combination distinguish 'Zancetopicsun' as a new and *Celosia* plant:

1. Compact and broadly upright plant habit.
2. Freely branching habit.
3. Dark green-colored leaves.
4. Freely flowering habit.
5. Bright yellow-colored flowers arranged on cristate-type inflorescences.
6. Good garden performance.

Plants of the new *Celosia* differ primarily from plants of the mutation parent, 'Zancetopicyel', in the following characteristics:

1. Plants of the new *Celosia* are more uniform than plants of 'Zancetopicyel'.
2. Flowers of plants of the new *Celosia* are brighter yellow in color than flowers of plants of 'Zancetopicyel'.

Plants of the new *Celosia* can be compared to plants of *Celosia argentea* 'Zancelpi', disclosed in U.S. Plant Pat. No. 19,300. In side-by-side comparisons, plants of the new *Celosia* and 'Zancelpi' differed primarily in the following characteristics:

1. Plants of the new *Celosia* were more compact than plants of 'Zancelpi'.
2. Plants of the new *Celosia* and 'Zancelpi' differed in flower color.

BRIEF DESCRIPTION OF THE PHOTOGRAPHS

The accompanying colored photographs illustrate the overall appearance of the new *Celosia* plant showing the colors as true as it is reasonably possible to obtain in colored reproductions of this type. Colors in the photographs may differ slightly from the color values cited in the detailed botanical description which accurately describe the colors of the new *Celosia* plant.

The photograph on the first sheet comprises a side perspective view of a typical flowering plant of 'Zancetopicsun' grown in a container.

The photograph on the second sheet is a close-up view of a typical flowering stem and upper surfaces of typical developing and fully expanded leaves of 'Zancetopicsun'.

DETAILED BOTANICAL DESCRIPTION

The aforementioned photographs and following observations, measurements and values describe plants grown during the spring in 9-cm containers in a glass-covered greenhouse in Rijsenhout, The Netherlands and under cultural practices typical of commercial production. During the production of the plants, day and night temperatures ranged from 20° C. to 22° C. Plants were pinched one time about 2.5 weeks after planting and were ten weeks old when the photographs and description were taken. In the following description, color references are made to The Royal Horticultural Society Colour Chart, 2001 Edition, except where general terms of ordinary dictionary significance are used.

Botanical classification: *Celosia hybrida* 'Zancetopicsun'.

Parentage: Naturally-occurring whole plant mutation of *Celosia hybrida* 'Zancetopicyel', not patented.

Propagation:

*Type*.—By cuttings.

*Time to initiate and develop roots, summer*.—About 12 days at temperatures about 21° C.

*Root description*.—Fine, fibrous; close to 199D in color.

*Rooting habit*.—Freely branching; dense.

Plant description:

*Plant form and growth habit*.—Herbaceous annual typically grown as a potted plant; compact and broadly upright plant habit; freely branching habit with about six lateral branches developing per plant; moderately vigorous.

*Plant height*.—About 25 cm.

*Plant width (spread)*.—About 24 cm.

*Lateral branches*.—Length: About 24 cm. Diameter: About 6 mm. Internode length: About 2 cm. Texture: Smooth, glabrous. Color: Close to 139D.

Foliage description:

*Arrangement*.—Alternate; simple.

*Length*.—About 10 cm to 15 cm.

*Width*.—About 2 cm to 5 cm.

*Shape*.—Elliptic.

*Apex*.—Acuminate.

*Base*.—Attenuate.

*Margin*.—Entire.

*Texture, upper and lower surfaces*.—Smooth, glabrous.

*Venation pattern*.—Pinnate.

*Color*.—Developing leaves, upper surface: Close to 137A. Developing leaves, lower surface: Close to 137B. Fully expanded leaves, upper surface: Close to 137A; venation, close to 149D. Fully expanded leaves, lower surface: Close to 138A; venation, close to 144B.

*Petiole length*.—About 2 cm to 3 cm.

*Petiole diameter*.—About 2 mm.

*Petiole texture, upper and lower surfaces*.—Smooth, glabrous.

*Petiole color, upper surface*.—Close to 149D.

*Petiole color, lower surface*.—Close to 144B.

Flower description:

*Flower type and flowering habit*.—Single elliptical flowers arranged in terminal and axillary spikes; cristate-type inflorescences; flowers face mostly upright; freely flowering habit, about 80 to 140 flowers per inflorescence and about 5,600 flowers developing per plant.

*Fragrance*.—None detected.

*Natural flowering season*.—Plants begin flowering about six weeks after planting; in the garden, plants flower continuously during the summer in The Netherlands.

*Postproduction longevity*.—Inflorescences last about two months on the plant; flowers persistent.

*Inflorescence height*.—About 4 cm to 6.5 cm.

*Inflorescence diameter*.—About 2.5 cm to 5 cm.

*Flower diameter*.—About 2 mm.

*Flower depth*.—About 6 mm.

*Flower buds*.—Length: About 3 mm. Diameter: About 1 mm. Shape: Elliptic. Color: Close to 158D.

*Petals*.—None observed.

*Sepals*.—Quantity per flower: Typically five. Length: About 5 mm. Width: About 2 mm. Shape: Lanceolate. Apex: Acute. Base: Attenuate. Margin: Entire. Texture, upper and lower surfaces: Smooth, glabrous. Color: When opening and fully opened, upper surface: Close to 158D; color does not fade with development. When opening and fully opened, lower surface: Close to 158D; color does not fade with development. Prophylls: Towards the apex, close to 18A; towards the base, close to 158D.

*Pedicels*.—Length: About 3 mm. Diameter: About 2 mm. Angle: About 45° from vertical. Strength: Weak; flexible. Texture: Smooth, glabrous. Color: Close to 150D.

*Reproductive organs*.—Stamens: Quantity per flower: Typically five. Filament length: About 1.5 mm. Filament color: Close to 150D. Anther length: About 2 mm. Anther color: Close to 177C. Pollen amount: Moderate. Pollen color: Close to 156D. Pistils: Quantity per flower: One. Pistil length: About 4 mm. Style length: About 2 mm. Style color: Close to 150D. Stigma color: Close to 160C. Ovary color: Close to 154D.

*Seeds*.—Length: About 1.5 mm. Diameter: About 1.5 mm. Color: Close to 202A.

Disease & pest resistance: Plants of the new *Celosia* have not been noted to be resistant to pathogens and pests common to *Celosia* plants.

Garden performance: Plants of the new *Celosia* have been observed to have good garden performance and tolerate rain, wind and temperatures ranging from about 5° C. to 35° C.

It is claimed:

1. A new and distinct *Celosia* plant named 'Zancetopicsun' as illustrated and described.

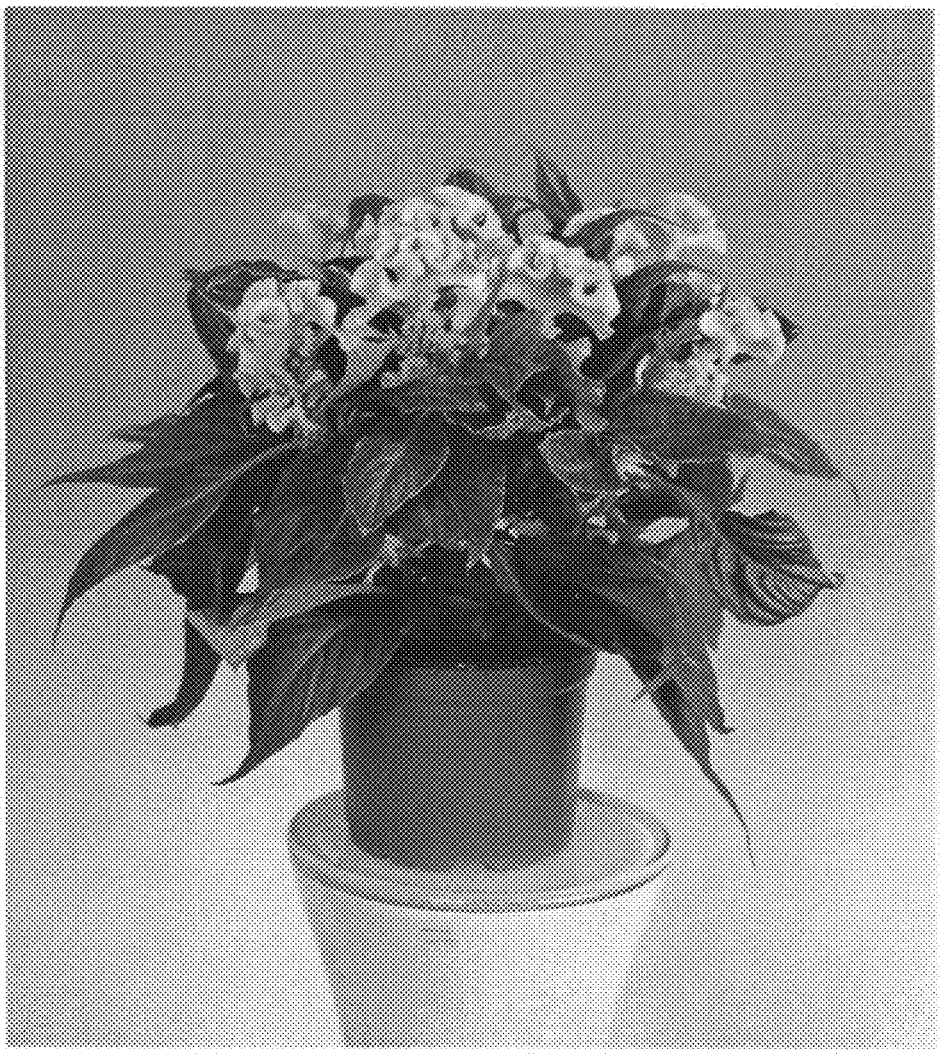

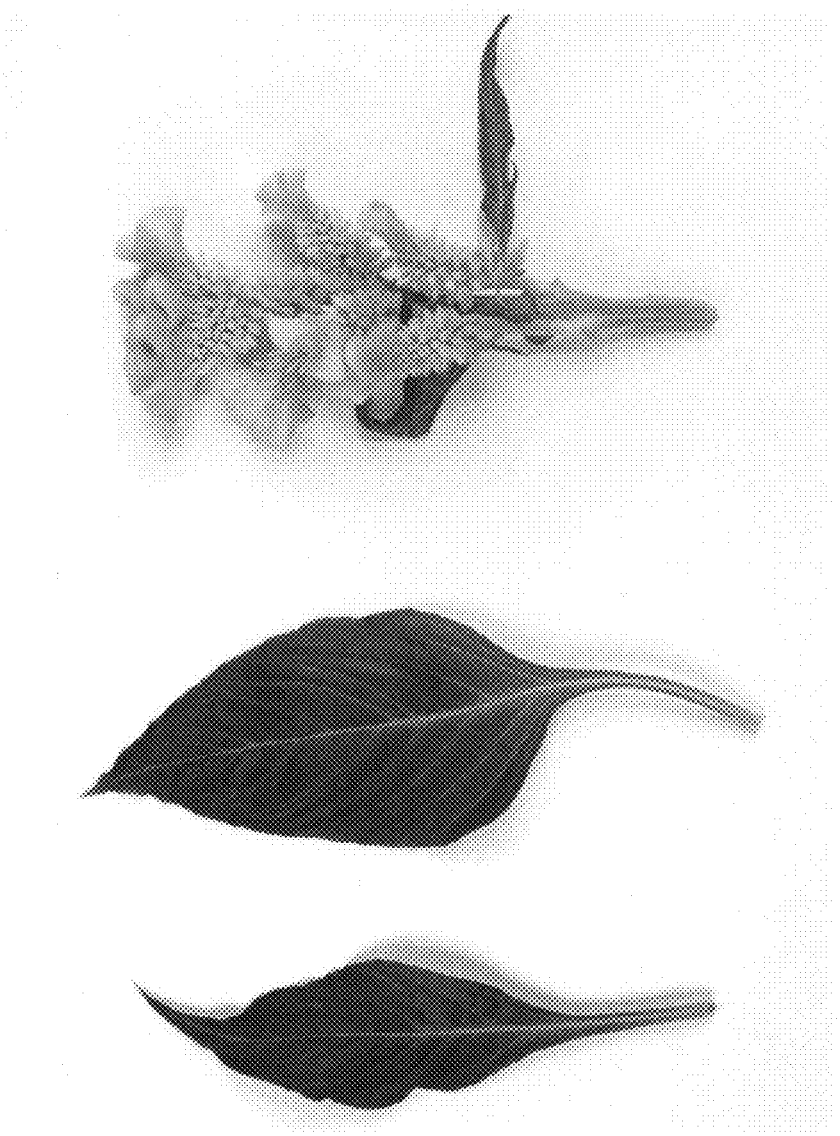

* * * * *